(12) United States Patent
Gutierrez et al.

(10) Patent No.: US 6,276,917 B1
(45) Date of Patent: Aug. 21, 2001

(54) POWDER PROCESSING APPARATUS

(75) Inventors: Emilio J. Gutierrez, New York, NY (US); Peter M. Hafermann, Yorba Linda; Matthew W. Phillips, Tustin, both of CA (US)

(73) Assignee: Botanicals International, Long Beach, CA (US)

( * ) Notice: Subject to any disclaimer, the term of this patent is extended or adjusted under 35 U.S.C. 154(b) by 0 days.

(21) Appl. No.: 09/239,104

(22) Filed: Jan. 28, 1999

(51) Int. Cl.[7] .................................................. B29B 9/16
(52) U.S. Cl. ............................ 425/237; 425/331; 425/352
(58) Field of Search ................................. 425/237, 331, 425/352, 544; 264/118

(56) References Cited

U.S. PATENT DOCUMENTS

| | | | |
|---|---|---|---|
| 4,659,299 | * 4/1987 | Pierik | 425/72 R |
| 4,721,448 | * 1/1988 | Irish et al. | 425/144 |
| 5,306,131 | * 4/1994 | Brotz | 425/201 |
| 5,308,566 | * 5/1994 | Huder | 264/118 |
| 5,598,770 | * 2/1997 | Campbell et al. | 99/487 |

* cited by examiner

*Primary Examiner*—Robert Davis
*Assistant Examiner*—Joseph S. Del Sole
(74) *Attorney, Agent, or Firm*—Oppenheimer, Wolff & Donnelly LLP

(57) ABSTRACT

A system is provided for pelletizing particulate raw matter having a first density, and thereafter subjecting the pellets to a milling process to obtain a powdered form of the particulate. During pelletizing steam can be added. The resulting powder is denser, or more granular or has better flow with less dust than the pre-pelletized particulate matter having the first density. The powderized particulate has applications for pharmaceutical, nutritional and herbal end products.

6 Claims, 2 Drawing Sheets

POWDER PROCESSING APPARATUS

BACKGROUND OF THE INVENTION

This invention relates to forming particulate powderized materials for use, particularly in the pharmaceutical, nutritional and dietary supplement industries. The invention is particularly concerned with providing an end product, which is denser, more granular and generates less dust with better flow than previously known products for these purposes. This is particularly valuable in that the end product has a minimum of, and in most cases no, fillers or diluents to obtain the desired end product, which is therefore substantially pure.

Traditional densification and dry granulation is performed mainly by the pharmaceutical industry using a roll compactor. An example of this is system known as the Chilsonator (™). The success of roll compaction is limited by the compactability or cohesiveness of the specific material. Frequently, the material requires preblending with compressible fillers and diluents in order to achieve compaction. Even with the most suitable fillers, roll compaction is frequently inefficient and slow because not all of the material gets compacted on the first pass through the rollers. Uncompacted material must be constantly recycled back through the machine until compacted. Compacted material forms a thin brittle ribbon which is then ground back into a powder of desired particle size. The resulting powder is normally higher in density or more compressible. The resulting powder however has fillers or diluents, which are generally undesirable.

An alternate way of accomplishing similar results is by using a tablet press to compress large tablets or slugs ("slugging") then milling them back into a powder. This format also has the disadvantage that there are diluents and fillers, which are generally undesirable.

There is, accordingly, a need to provide for improved system of powderized products which can provide enhanced flow properties, and better compaction and compressibility. There is a need to provide such a system which can permit for the production of end products, for instance, in the form bulk powders, or powders for tableting or encapsulating in gelatin capsules or the like.

SUMMARY OF THE INVENTION

By this invention the Applicants minimize the disadvantages of known techniques for processing raw material products. The Applicants provide a system for forming powderized or granulated products of higher density, with less dust, better granularity and better flow characteristics.

According to the invention, there is a system as provided for pelletizing particulate raw matter, and thereafter subjecting the pellets to a milling process to obtain a powdered form of the particulate. During pelletizing steam can be added. The resulting powder is denser, more granular and has better free flow properties than the pre-pelletized particulate matter. The powderized particulate has applications for pharmaceutical, nutritional and dietary supplement end products.

A system is provided for pelletizing particulate raw matter having a first density, and thereafter subjecting the pellets to a milling process to obtain a powdered form of the particulate. During pelletizing steam can be added. The resulting powder is denser, more granular and has better flow than the pre-pelletized particulate matter having the first density. The powderized particulate has applications for pharmaceutical, nutritional and dietary supplement finished products.

Apparatus for processing products for increasing the density of particulate matter in a powderized form comprises feed means for directing particulate matter into a pelletizing mill, the particulate matter being in a first powderized form and having a first density. A pelletizing mill generates pellets of the particulate matter. The pellets are then milled into a second powderized form, whereby the second powderized form of the particulate has a greater density than the first density. This is achieved in a manner where the formed pellet substantially exclude diluents or fillers.

During pellitization, some products required the introduction of saturated steam at a selected temperature, pressure and condensation characteristic. There is at least about 95% substantially pure saturated steam under a pressure of about 40 to about 80 PSI at about a temperature of about 180° F. to about 400° F. This hydrates the particulate matter at a temperature of about 80° F. to 200° F. and thereby add about 1% moisture to the particulate matter. The product with increased moisture content is forced under pressure through a spinning perforated dye of a predetermined dimension thereby to obtain a pellet of a selected size, the forcing through the die being effected selectively by dual inner rotating roller means.

There is a pre-milling step for processing raw materials to obtain a particulate matter for feeding into the pelletizing mill. The pellets exposed to steam are cooled to a substantially ambient temperature prior to being milled. A cooler at an outlet from the pelletizing mill permits ambient air to pass through a bed containing pellets discharged from the pelletizing mill.

The processed product is relatively coarser, capable of improved flow and relatively more compressible than the particulate matter. The powderized product in the second form has relatively greater granularity than the particulate matter in the first form. In the second powderized form the product can be made into, selectively, bulk powders such as teas or sports drinks or tablets, and capsules, and selectively have at least one other ingredient.

The invention is further described with reference to the accompanying drawings.

BRIEF DESCRIPTION OF THE DESCRIPTION DRAWINGS

DETAILED DESCRIPTION OF THE PREFERRED EMBODIMENT

Figure 1:
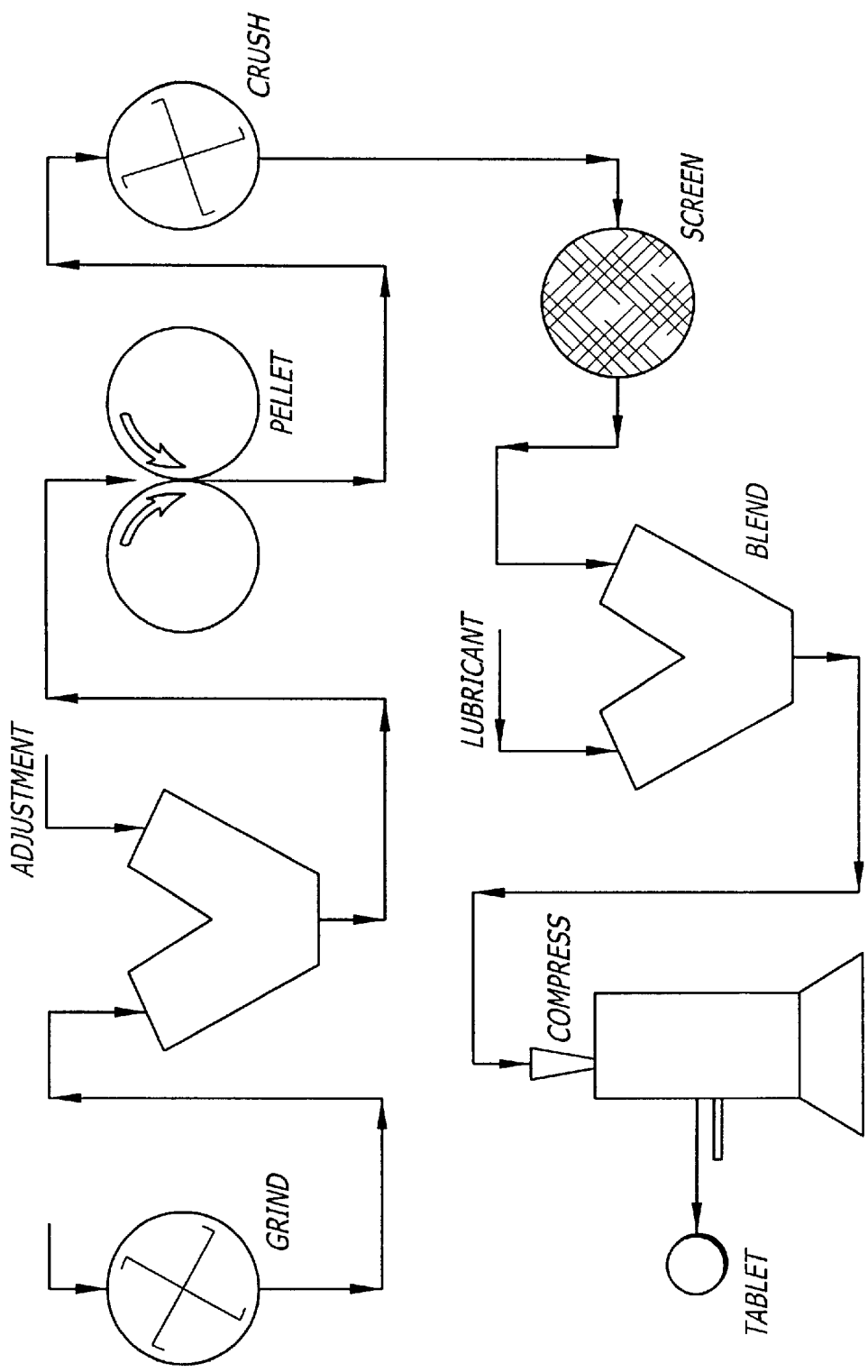
FIG. 1 is a flow diagram illustrating a prior art method to form granular materials and tablets according to a dry granulation technique.
Figure 2:
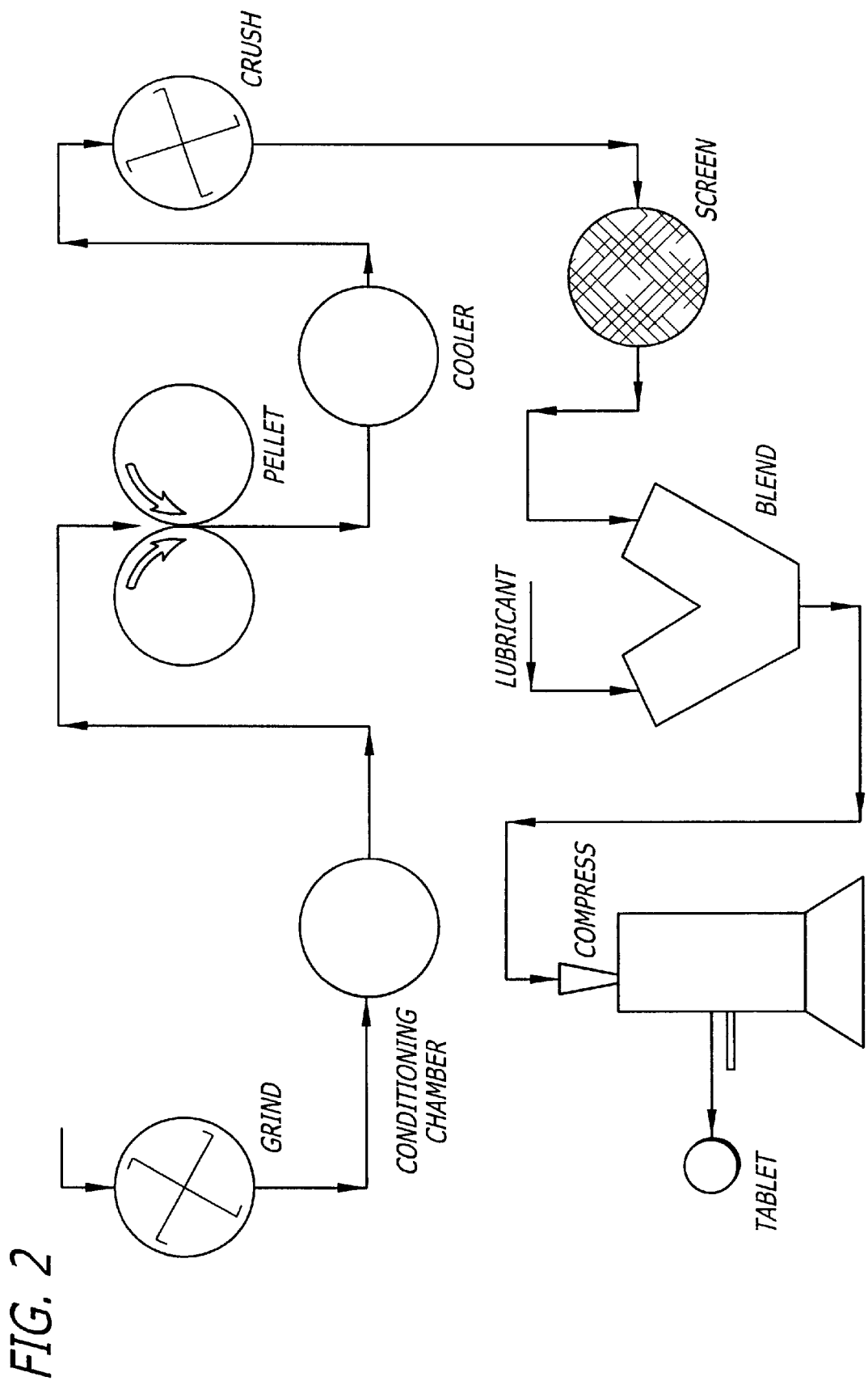
FIG. 2 is a flow diagram illustrating a method to form granular materials and tablets according to a dry granulation system of the invention.

The Applicants describe by example a system, apparatus and method for performing the process of the invention. The invention includes the apparatus for performing the process under the process, and also products made by the apparatus.

The system provides for pelletizing particulate raw matter, and thereafter subjecting the pellets to a milling process to obtain a powdered form of the particulate. During pelletizing steam is added. The resulting powder is denser, more granular and has better flow than the pre-pelletized particulate matter. The powderized particulate end product has applications for pharmaceutical, nutritional and herbal end products.

There is apparatus and a method for processing products for increasing the density of particulars in a powderized form. Feed means directs particulate matter into a pelletizing mill. The particulate matter has a first density. The pelletizing mill forms pellets of the particulate matter. Thereafter the pellets are milled into a powderized form. The powderized form of the particulate has a second density which is a greater density than the first density.

The steam fed pellet mill is used to increase the density of powders, create or enlarge granules, control particle size, enhance flow properties, decrease dust and create granulations without using diluents or fillers. The products are particularly, but not exclusively, applicable to making end products for the pharmaceutical, nutritional or dietary supplement industries.

General Description of Pelletizing Process:

A pellet mill originally designed to make animal feed is used to control particle size, increase a product's density, or add granularity and decrease dust by forming a pellet and milling it back into powder form.

Particulate product of predetermined particle size is fed into a conditioning chamber where it can be exposed to saturated steam of controlled temperature, pressure and condensation. The steam increases the product's inherent moisture content and compressibility. This benefit is normally only obtained through the use of compressible fillers in the traditional dry granulation methods of the pharmaceutical industry.

To form the pellet, the conditioned product is forced at extreme pressure through a spinning perforated die of preselected dimension by two rotating inner rollers. Nearly all of the material compresses into pellets with a minimal amount of product "fines". The lack of "fines" increases the pellet mill's overall output because there is no need to recycle a large percentage of the product back through the machine. Increased product throughput with minimal recycling makes pelletizing much more cost effective than alternate dry granulation means.

Pellets are quickly cooled to room temperature and milled to a specific particle size range based on the intended application of the product. The resulting powder is coarser, denser, better flowing with less dust, and more compressible or compactable. This makes it ideal for the manufacturing of pharmaceutical dosage forms such as tablets and capsules or nutritional powder drink mixes. This can be a powder blend.

Pre-milling—(Preparing the raw material for pelletizing)

Using a hammermill or equivalent milling device for whole plants, roots, leaves, dried fruits or pharmaceutical actives are ground to produce a fine homogeneous powder. Traditionally, the pellet mill is used to manufacture products for the grain or animal feed industry. In this prior art application, molasses, starches and fats are added at the conditioning chamber along with steam to help the material bind together. Required particle size is only about 700 microns (25 mesh) because the binders help hold the pellet together.

Binders used to make animal feed are not desirable in the pelletizing of herbal or pharmaceutical products according to the present invention. Without binders, the particle size of the starting raw material becomes extremely critical. Products are ground to finer particle size, ranging from 100 to 1300 microns (14 to 150 mesh), to increase the surface area and create more binding sites within each individual particle. The compacting step requires more shear force because it is dependent on steam or the product's own compressible properties.

Steam and the Conditioning Chamber

Inside the conditioning chamber, the powder bed is typically penetrated by 95% to 100% pure saturated steam with a typical pressure of 40 to 80 PSI. Steam temperature may range between 180° F. to 400° F. while it heats and hydrates the powder to a temperature of 80° F. to 200° F. adding approximately 1% moisture. Products that are naturally compressible solely by shear force, require no steam to form a pellet.

Feeding the Pellet Mill

The rate at which the conditioning chamber feeds the pellet mill is controlled by the amount of steam and the required heat exposure to form good pellets. Feeding rate is also controlled by resistance created inside the die while pelletizing, product flow and force needed to compress. Ultimately, an optimum flow rate setting is determined for each individual product.

The Effect of Product Variability on the Pelletizing Process

Certain products with good compressible properties such as ginger root powder can be pelletized with little or no steam depending on the individual product lot.

Products which contain a high percentage of fibrous matter, such as Siberian Ginseng, require substantial exposure to steam and greater force to compact.

Products with low melting points that compact with minimal force require a relieved die that subjects the product to less shear force and friction. These products will also form pellets without the need for steam.

Characteristics of a Typical Pellet Mill

25 HP Motor 1800 RPM

Die Speed 230 RPM

Mixer Speed 500 RPM

12' die, standard, 3.94" wide 149 in$^2$ Working Area

Density of typical pellet 1.3 g/mL

Length of pellets can vary between ¼" to 2" depending on the blade setting

CPM (California Pellet Mills), Series 1100 Pellet Mill or Series 3000 Pellet Mill with Counter flow Coolers.

Cooler

Heated pellets are discharged from the pellet mill into the cooler. The cooler fan draws ambient air upward through the pellet bed. The pellets are cooled gradually as they move through the rising air current. To prevent cooling shock, cold air comes in contact with cooled hardened pellets while incoming hot pellets come in contact with air preheated by the warm pellets before it.

Specification in Milling Pellets—Controlling Particle Size and Density

Pellets are milled to meet a wide range of specifications. Typical ranges can be anywhere between 100 and 1300 microns or 100% through 14 to 150 mesh.

For raw materials that are going to be compressed into tablets, a normal requirement would be 100% through a 14 mesh with a bell shape standard distribution of particle sizes and perhaps no more than 40% through a 100 mesh. This would be difficult to produce without the pelletizing process because most raw material powders would be either too fine or of a homogeneous particle size. The granularity created by the pelletizing process is what makes the product suitable for tablet compression.

For raw materials that are going to be placed inside gelatin capsules, a typical particle size requirement can be 100% through a 60 or 80 mesh. Powders that are just milled and do not undergo the pelletizing process can sometimes be as fine as 100% through 200 mesh. These products are dusty and difficult to work with because of their poor flow characteristics. The pelletizing process would make this product coarser and better flowing.

Added density and no fillers allow product formulators design dosage forms with more consumer appeal. Tablets and capsules are smaller, more concentrated or undiluted and easier to swallow.

Advantages

Particle size shift to bigger screens on the sieve analysis test—more coarse particles result and less dust or fines.

Better particle size distribution—not all particles are nearly the same size.

Same moisture—Steam does not add additional moisture to the final product.

Increased density—Density increase in excess of 100% is possible on some products.

Increased fill weight on gelatin capsules—More product fits in a small capsule.

Better flow—Less tablet or capsule weight variability through better flow and compactability.

More granularity—Some products are now compressible without compressible fillers.

Increased manufacturing efficiency—Pellet mill offers more product throughput than traditional means of the pharmaceutical industry.

Applicants now set out in Table 1 some example products as illustrated. For each of these raw material products, there is set out the normal powder characteristics and also the pelletized powder characteristics, the latter being in terms of the current invention.

TABLE 1

HD Powder Line Example Products

| | Density | Loose | % Gain | Tapped | % Gain | Mesh Size |
|---|---|---|---|---|---|---|
| Ginkgo Leaf HD | Normal Powder | 0.29 | | 0.43 | | |
| | Pelletized Powder | 0.43 | 48% | 0.56 | 30% | 60 |
| Korean Ginseng Root HD | Normal Powder | 0.44 | | 0.59 | | |
| | Pelletized Powder | 0.56 | 27% | 0.75 | 27% | 60 |
| *Echinacea Purpurea* Herb HD | Normal Powder | 0.22 | | 0.40 | | |
| | Pelletized Powder | 0.50 | 127% | 0.70 | 75% | 60 |
| Gota Kola Herb HD | Normal Powder | 0.35 | | 0.50 | | |
| | Pelletized Powder | 0.56 | 60% | 0.80 | 60% | 60 |
| *Valerian Officinalis* Root HD | Normal Powder | 0.47 | | 0.62 | | |
| | Pelletized Powder | 0.64 | 36% | 0.80 | 29% | 40 |
| Siberian Ginseng Root HD | Normal Powder | 0.45 | | 0.61 | | |
| | Pelletized Powder | 0.68 | 51% | 0.90 | 48% | 60 |
| Feverfew Herb HD | Normal Powder | 0.28 | | 0.41 | | |
| | Pelletized Powder | 0.53 | 89% | 0.70 | 71% | 40 |
| Astragalus Root HD | Normal Powder | 0.36 | | 0.57 | | |
| | Pelletized Powder | 0.57 | 58% | 0.77 | 35% | 40 |
| Red Raspberry Leaves HD | Normal Powder | 0.31 | | 0.49 | | |
| | Pelletized Powder | 0.38 | 23% | 0.56 | 14% | 80 |

TABLE 1-continued

HD Powder Line Example Products

| | Density | Loose | % Gain | Tapped | % Gain | Mesh Size |
|---|---|---|---|---|---|---|
| Foti Root HD | Normal Powder | 0.49 | | 0.62 | | |
| | Pelletized Powder | 0.66 | 35% | 0.80 | 29% | 40 |
| Alfalfa Herb HD | Normal Powder | 0.19 | | 0.34 | | |
| | Pelletized Powder | 0.43 | 126% | 0.53 | 56% | 40 |
| Ginger Root HD | Normal Powder | 0.41 | | 0.61 | | |
| | Pelletized Powder | 0.54 | 32% | 0.75 | 23% | 20 |
| Black Cohosh Root HD | Normal Powder | 0.55 | | 0.58 | | |
| | Pelletized Powder | 0.61 | 11% | 0.73 | 26% | 40 |
| Cat's Claw Root HD | Normal Powder | 0.40 | | 0.58 | | |
| | Pelletized Powder | 0.54 | 35% | 0.70 | 21% | 60 |
| Nettle Root HD | Normal Powder | 0.35 | | 0.48 | | |
| | Pelletized Powder | 0.52 | 49% | 0.66 | 38% | 80 |
| St. John's Wort Herb HD | Normal Powder | 0.34 | | 0.42 | | |
| | Pelletized Powder | 0.48 | 41% | 0.52 | 24% | 40 |
| *Echinacea Angustifolla* Root HD | Normal Powder | 0.25 | | 0.33 | | |
| | Pelletized Powder | 0.49 | 96% | 0.57 | 73% | 40 |
| Red Clover Tops HD | Normal Powder | 0.30 | | 0.43 | | |
| | Pelletized Powder | 0.36 | 20% | 0.52 | 21% | 80 |

The Applicants further set out other exemplary data showing the effectiveness of the product in terms of the invention.

In Table 2 a prior art normal powder technique is set out with its effective analysis. The comparative table for the same product is set out in terms of the present invention in Table 4. Compare the sections labeled Sieve Analysis and Tapped Density.

In Table 3 sets out a normal powder analysis for a different product in terms of the prior art. Table 5 sets out an analysis of the same product in terms of the invention. Also, compare the sections labeled Sieve Analysis and Tapped Density.

TABLE 2

Normal Powder (Prior Art)
SIEVE ANALYSIS

| Test Description | | Result |
|---|---|---|
| % THROUGH US | #40 SCREEN | 100.0000 |
| % THROUGH US | #60 SCREEN | 98.5000 |
| % THROUGH US | #80 SCREEN | 58.9000 |
| % THROUGH US | #100 SCREEN | 48.3000 |
| % THROUGH US | #140 SCREEN | 33.6000 |

TABLE 3

Normal Powder (Prior Art)
SIEVE ANALYSIS

| Test Description | | Result |
|---|---|---|
| % THROUGH US | #40 SCREEN | 100.0000 |
| % THROUGH US | #60 SCREEN | 99.8000 |
| % THROUGH US | #80 SCREEN | 85.0000 |
| % THROUGH US | #100 SCREEN | 74.5000 |
| % THROUGH US | #140 SCREEN | 56.0000 |

TABLE 4

Pelletized Powder (Invention)
SIEVE ANALYSIS

| Test Description | | Result |
|---|---|---|
| % THROUGH US | #40 SCREEN | 100.0000 |
| % THROUGH US | #60 SCREEN | 99.3000 |
| % THROUGH US | #80 SCREEN | 68.3000 |
| % THROUGH US | #100 SCREEN | 55.0000 |
| % THROUGH US | #140 SCREEN | 30.9000 |

TABLE 5

Pelletized Powder (Invention)
SIEVE ANALYSIS

| Test Description | | Result |
|---|---|---|
| % THROUGH US | #40 SCREEN | 100.0000 |
| % THROUGH US | #60 SCREEN | 98.1000 |
| % THROUGH US | #80 SCREEN | 70.7000 |
| % THROUGH US | #100 SCREEN | 58.2000 |
| % THROUGH US | #140 SCREEN | 37.3000 |

Many other forms of the invention exist, each differing from the other in matters of detail only. For instance different feed means can be used for directing particulate matter into the pelletizing mill. Different consistencies of the particulate matter in its first powderized form and first density are possible. Different formats of pelletization are possible. Different pellet mill manufacturers and different pellet mill sizes and die specifications are possible.

Although ideally there are no diluents or fillers, it is possible under certain preferred formulations to add a degree of such products. The introduction of steam into the pellet mill may be optional, as indeed are different pressures and temperatures possible. Cooling of the pellets to a substantially ambient temperature prior to being milled by the milling means can be optional. Other cooling temperatures are possible.

The increased moisture content can be added by techniques other than forced pressure through a spinning perforated die, and other than by forcing material through the die being effected selectively by inner rotating roller means. The pellets can vary in size, consistency and shape. The milled pellets output in a powderized form can have sizes different to a size between about 100 to about 800 microns. Also, the size of the output powder can be different to a size where about 100% of the powderized product is passable through a 14 mesh.

The end products of the method and/or apparatus may be for use in industries other than for the pharmaceutical, nutritional or herbal end products.

The invention is to be determined solely by the following claims.

What is claimed is:

1. Apparatus for processing products for increasing the density of particulate matter in a powderized form consisting essentially of:

means for pre-milling for processing raw materials to obtain a particulate matter for feeding into a pellet mill;

feed means for directing the particulate matter into the pellet mill, the particulate matter being in a first powderized form and having a first density;

the pellet mill for generating pellets of the first particulate matter;

means to introduce steam into the pellet mill during the formation of pellets;

means to cool the pellets to a substantially ambient temperature; and means for milling the pellets into a second powderized form, whereby the second powderized form of the particulate has a greater density than the first density.

2. Apparatus as claimed in claim 1 wherein the means to introduce steam includes means for applying saturated steam at a selected temperature and pressure and condensation characteristic to the pellet mill during pelletization thereby to increase the moisture content of the product.

3. Apparatus as claimed in claim 2 wherein the pellet mill includes a spinning perforated die of a predetermined dimension thereby to obtain a pellet of a selected size and the product is forced through the die by rotating roller means.

4. Apparatus as claimed in claim 1 wherein the means to introduce steam includes a conditioning chamber, and including means in the conditioning chamber for penetrating the particulate material in the conditioning chamber by at least 95% substantially pure saturated steam under a pressure of about 40 to about 80 PSI at a temperature of about 180° F. to about 400° F. thereby to hydrate the particulate matter at a temperature of about 80° F. to 200° F. and thereby add about 1% moisture to the particulate matter.

5. Apparatus as claimed in claim 1 wherein the means for milling the pellets produces the second powderized form having an approximate size between about 100 to about 1300 microns, or of a size where about 100% of the powderized product is between a 14 mesh to a 150 mesh.

6. Apparatus as claimed in claim 1 wherein the means for milling the pellets produces the second powderized form having a particle size permitting about 100% through a 60 to 80 mesh.

* * * * *